(12) United States Patent
Nakao

(10) Patent No.: US 7,648,514 B1
(45) Date of Patent: Jan. 19, 2010

(54) DEEP ENDOSCOPIC STAPLE AND STAPLER

(75) Inventor: Naomi L. Nakao, New York, NY (US)

(73) Assignee: Granit Medical Innovation, LLC, New York, NY (US)

( * ) Notice: Subject to any disclaimer, the term of this patent is extended or adjusted under 35 U.S.C. 154(b) by 354 days.

(21) Appl. No.: 11/715,657

(22) Filed: Mar. 8, 2007

Related U.S. Application Data

(60) Provisional application No. 60/780,359, filed on Mar. 8, 2006.

(51) Int. Cl.
*A61B 17/10* (2006.01)

(52) U.S. Cl. .................. 606/142; 606/151; 227/175.1

(58) Field of Classification Search ............ 227/175.1, 227/181.1, 175.3, 175.2; 606/206, 142, 143, 606/157, 151; 29/243.56, 243.57, 243.58
See application file for complete search history.

(56) References Cited

U.S. PATENT DOCUMENTS

| | | | | |
|---|---|---|---|---|
| 3,882,854 A | * | 5/1975 | Hulka et al. ................. | 600/104 |
| 4,152,920 A | * | 5/1979 | Green ..................... | 72/409.05 |
| 4,241,861 A | * | 12/1980 | Fleischer ................... | 227/135 |
| 4,367,746 A | * | 1/1983 | Derechinsky ............... | 606/142 |
| 4,408,603 A | * | 10/1983 | Blake et al. ................ | 606/143 |
| 4,662,373 A | * | 5/1987 | Montgomery et al. ....... | 606/143 |
| 4,821,939 A | * | 4/1989 | Green ......................... | 227/19 |
| 5,015,249 A | * | 5/1991 | Nakao et al. ................ | 606/142 |
| 5,049,153 A | * | 9/1991 | Nakao et al. ................ | 606/151 |
| 5,125,553 A | * | 6/1992 | Oddsen et al. ............. | 227/175.1 |
| 5,222,961 A | * | 6/1993 | Nakao et al. ................ | 606/143 |
| 5,304,183 A | * | 4/1994 | Gourlay et al. ............. | 606/142 |
| 5,306,283 A | * | 4/1994 | Conners ..................... | 606/151 |
| 5,354,304 A | * | 10/1994 | Allen et al. ................. | 606/142 |
| 5,366,134 A | * | 11/1994 | Green et al. ............. | 227/176.1 |
| 5,540,240 A | * | 7/1996 | Bauer ......................... | 128/898 |
| 5,626,587 A | * | 5/1997 | Bishop et al. ............... | 606/143 |
| 5,626,592 A | * | 5/1997 | Phillips et al. .............. | 606/157 |
| 5,713,911 A | * | 2/1998 | Racenet et al. .............. | 606/157 |
| 5,972,003 A | * | 10/1999 | Rousseau et al. ............ | 606/142 |
| 6,024,748 A | * | 2/2000 | Manzo et al. ................ | 606/153 |
| 6,315,183 B1 | * | 11/2001 | Piraka ..................... | 227/176.1 |
| 6,325,810 B1 | * | 12/2001 | Hamilton et al. ............ | 606/151 |
| 6,443,973 B1 | * | 9/2002 | Whitman ..................... | 606/219 |
| 6,446,854 B1 | * | 9/2002 | Remiszewski et al. ... | 227/175.1 |
| 6,554,844 B2 | * | 4/2003 | Lee et al. ..................... | 606/130 |

(Continued)

*Primary Examiner*—Paul R Durand
(74) *Attorney, Agent, or Firm*—R. Neil Sudol; Henry D. Coleman; William J. Sapone

(57) ABSTRACT

A medical device includes an actuator handle, an elongate flexible inner tubular member operatively connected at one end to the handle, two jaws pivotably mounted to a distal end of the inner tubular member and biased to an open configuration, and an elongate flexible outer tubular member operatively connected at one end to the handle and slidably surrounding the inner tubular member. The outer tubular member is provided at a distal end with two cutouts or open slots opposed to one another to define a pair of longitudinally extending opposed fingers. The fingers are engageable with respective ones of the jaws to pivot the jaws towards one another during a distally directed stroke of the outer tubular member so that the jaws assume a closed configuration. The cutouts or open slots are disposed alongside the jaws in the closed configuration thereof to provide clearance for tissue material grasped in and protruding laterally from the jaws.

12 Claims, 21 Drawing Sheets

U.S. PATENT DOCUMENTS

| | | | |
|---|---|---|---|
| RE38,445 E * | 2/2004 | Pistl et al. | 606/143 |
| 6,786,382 B1 * | 9/2004 | Hoffman | 227/178.1 |
| 6,964,363 B2 * | 11/2005 | Wales et al. | 227/175.1 |
| 7,028,878 B2 * | 4/2006 | Bauer | 227/175.1 |
| 7,055,731 B2 * | 6/2006 | Shelton et al. | 227/176.1 |
| 7,105,000 B2 * | 9/2006 | McBrayer | 606/143 |
| 7,168,604 B2 * | 1/2007 | Milliman et al. | 227/176.1 |
| 2002/0111621 A1 * | 8/2002 | Wallace et al. | 606/41 |
| 2005/0216036 A1 * | 9/2005 | Nakao | 606/142 |

* cited by examiner

FIG. 9

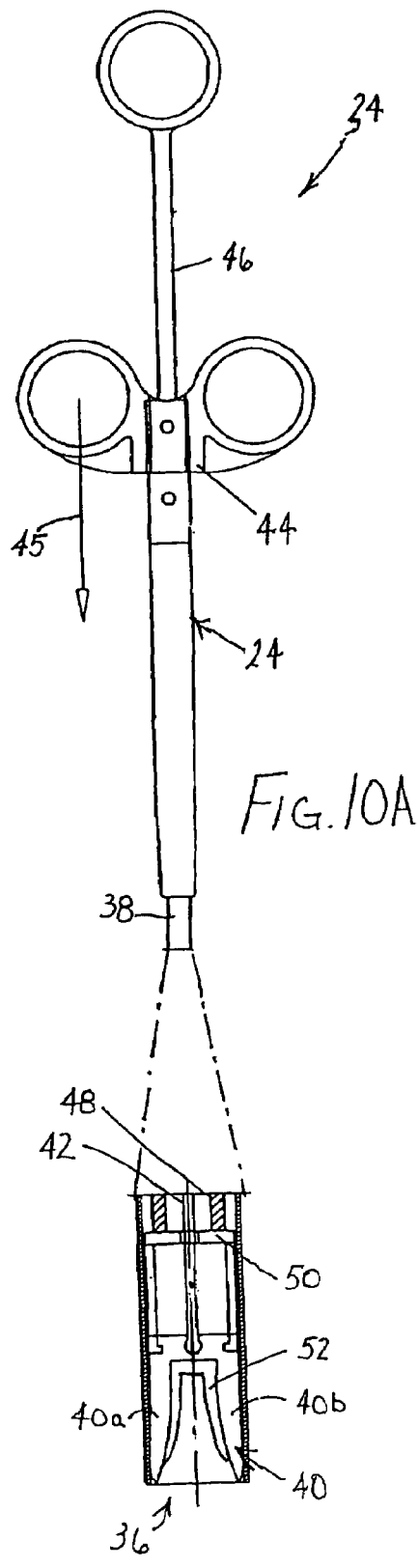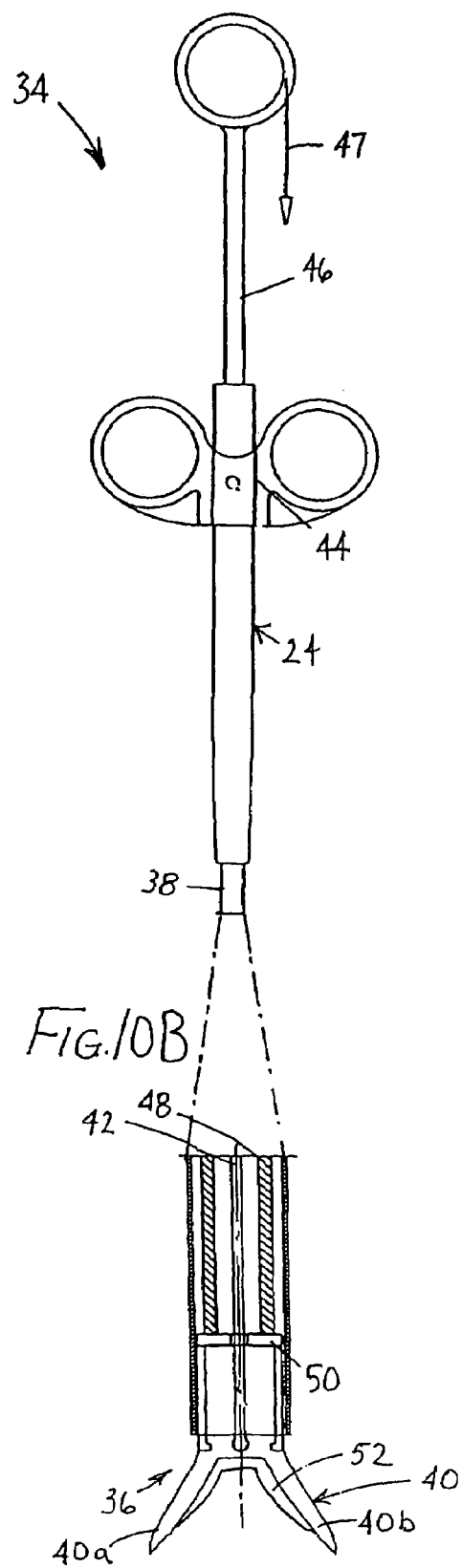
FIG. 10A
FIG. 10B

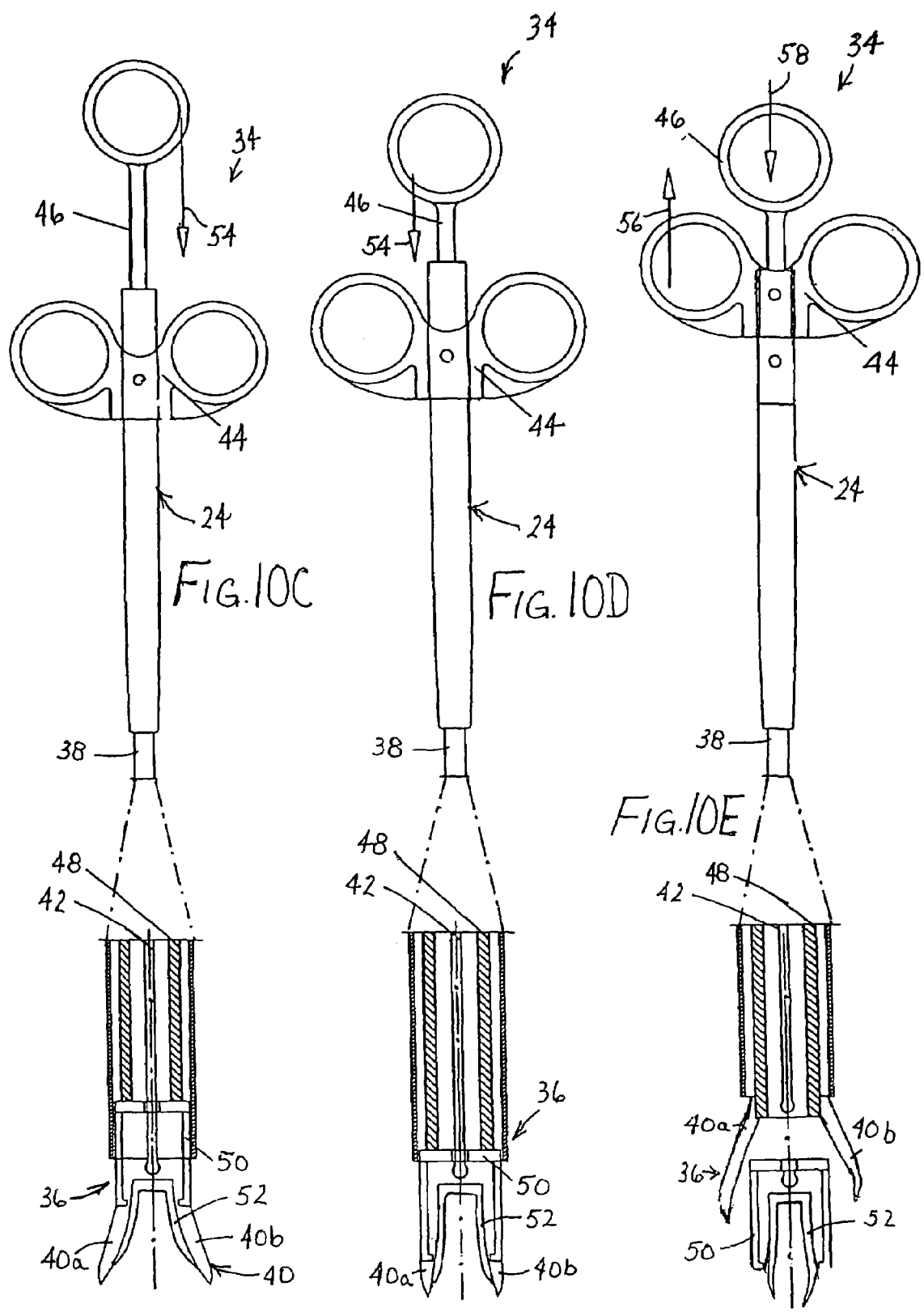

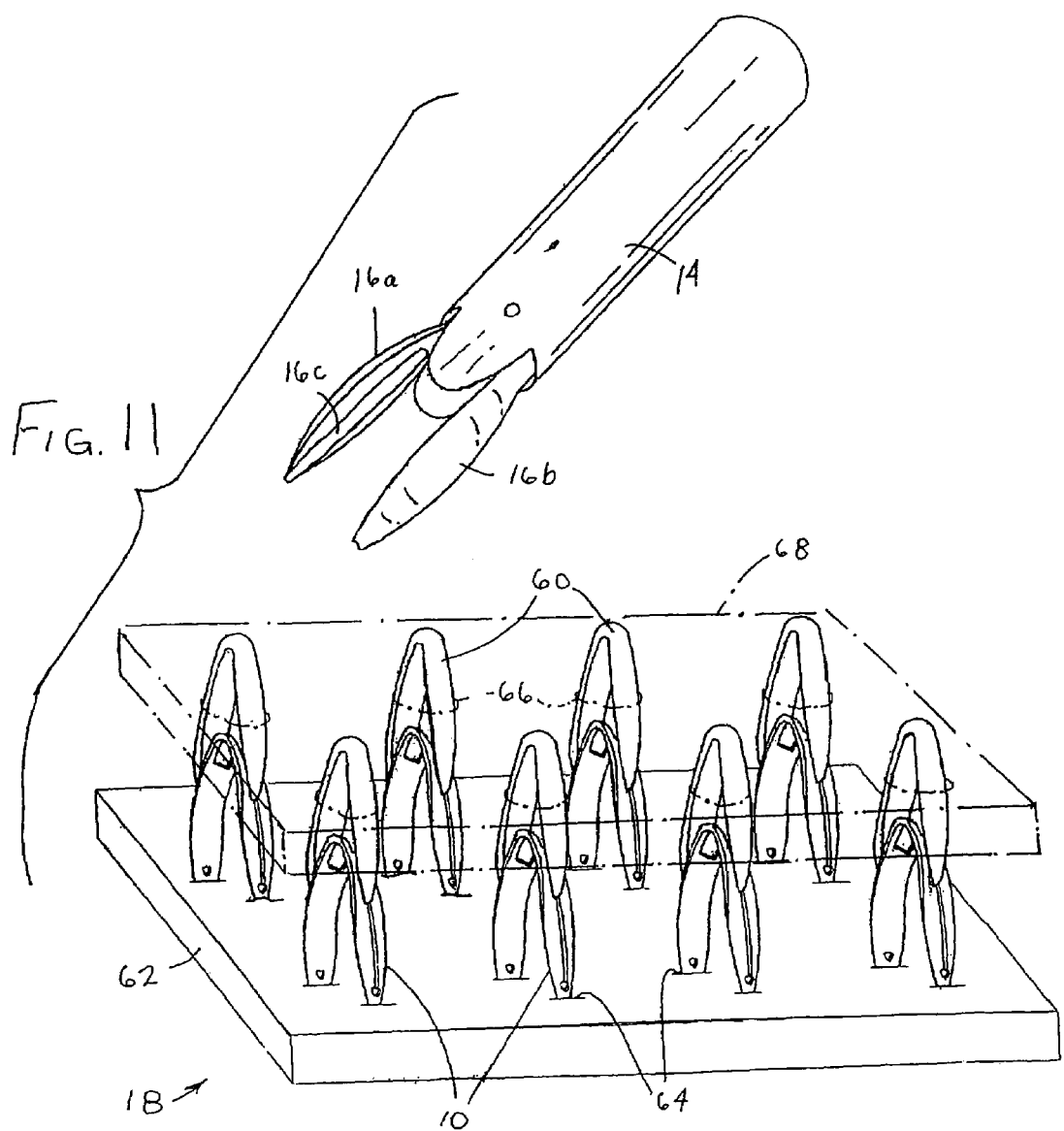

DEEP ENDOSCOPIC STAPLE AND STAPLER

CROSS-REFERENCE TO RELATED APPLICATION

This application claims the benefit of U.S. Provisional Patent Application No. 60/780,359 filed Mar. 8, 2006.

FIELD OF THE INVENTION

The present invention relates to endoscopy and, more particularly, to a staple and a device used to secure or staple tissue inside the human body with said staple and device working in conjunction with a flexible endoscope.

BACKGROUND OF THE INVENTION

Surgeons have developed a number of methods and techniques to treat a variety of medical anomalies in the abdomen and gastrointestinal tract. These procedures often involve stapling and must be performed during open surgery or rigid laparoscopic surgery because there is no device or reliable method for placing staples using flexible endoscopes. Suturing has the same current limitations and as such the medical community is unable to perform surgical procedures via natural body openings using flexible endoscopes. Surgical procedures for removing diseased organs, gastric bypass surgery performed in morbidly obese patients, and a variety of other surgical procedures must be performed during open or laparoscopic surgery.

Providing the physicians with a flexible stapling device to be used in conjunction with a flexible endoscope would significantly reduce the length and complexity of the surgery. Consequently, morbidity and mortality would be reduced; hospital stay shortened, and cost savings provided. Because flexible endoscopic procedures are typically performed under conscious sedation and are much less invasive, they are naturally less traumatic to the body. Convalescence is significantly shortened, postoperative pain is virtually eliminated and patients are ambulatory within hours after an endoscopic procedure.

The only means of treating a problem that requires surgery in the abdomen is through open or laparoscopic surgery. Bypass and gastric restrictive surgery for the morbidly obese patient is being performed during open or laparoscopic surgery. These operations take five to seven hours and are performed under general anesthesia. The recovery typically takes six weeks to three months if the operation is successful. Recently, a new procedure has been introduced during which a band is placed around the stomach. This operation is less complex than the abovementioned procedures but is also being performed through open or laparoscopic means.

These complex and invasive surgical procedures require general anesthesia, surgical incisions, multiple days in the hospital, and significant use of medication for postoperative pain and lengthy periods of convalescence. Surgical procedures to treat morbidly obese patients have a high incidence of complications and thus limit the number of patients that can benefit from these procedures. These operations are currently performed through a large abdominal incision. The physician excludes or closes off a large portion of the stomach. In addition, a portion of the small intestine is bypassed, and a new connection to the stomach is made. Oftentimes the patient has had prior surgery causing adhesions, which bind the intestines together. The surgeon has to dissect these adhesions and free the bowel in order to get to the operative site. This procedure is quite difficult, and has to be performed before the actual bypass and gastric stapling operation has even begun. This surgery can also be performed laparoscopically. However, while the incisions are smaller, the abdomen is filled with a large amount of gas in order to distend it and enable the surgeon to perform the operation. The surgery is more difficult and typically takes two to three hours longer than the open operation. This requires longer anesthesia time increasing the danger to the patient. The distended abdomen impinges on the patient's lungs decreasing breathing capacity and adding morbidity. While this is a less invasive procedure than open surgery, it still entails significant complications and lengthy patient convalescence. Furthermore, because the surgery takes longer than open surgery, risk to the patient is increased from prolonged general anesthesia. The less traumatic banding procedure is less complicated; however, reports of band slippage and postoperative infection exist. In addition, results have been poor.

OBJECTS OF THE INVENTION

It is an object of this invention to provide a medical instrument for closing openings internal to a patient's body, utilizing flexible or rigid endoscopes inserted into the body primarily, though not exclusively, through existing body orifices.

It is another object of the invention to provide such an instrument for closing openings internal to a patient's body, which is quicker, safer and less invasive to use than conventional surgical procedures, thereby, significantly reducing patient morbidity and mortality.

It is a further object of this invention to provide such an instrument with a staple for closing or clamping tissue within the body that can be passed through a flexible endoscope.

It is a more specific object of this invention to provide a staple delivery instrument that can be used in conjunction with flexible and rigid endoscopes with a working channel diameter no larger than 3.8 millimeters.

It is yet another object of this invention to provide a long, flexible staple delivery device that can be passed deep into the organ to be operated upon.

It is also an object of this invention to provide a such a device for deploying a staple that will enter into the organ deeply enough to hold the desired tissues together, and with a closure strong enough to keep these tissues securely affixed to one another.

These and other objects of the invention will be apparent from the drawings and descriptions herein. Every object of the invention is believed to be attained by at least one embodiment of the invention. However, there is not necessarily any single embodiment that achieves all of the objects of the invention.

SUMMARY OF THE INVENTION

A medical device in accordance with the present invention comprises an actuator handle, an elongate flexible inner tubular member operatively connected at one end to the handle, two jaws pivotably mounted to a distal end of the inner tubular member and biased to an open configuration, and an elongate flexible outer tubular member operatively connected at one end to the handle and slidably surrounding the inner tubular member. The outer tubular member is provided at a distal end with two cutouts or open slots opposed to one another to define a pair of longitudinally extending opposed fingers. The fingers are engageable with respective ones of the jaws to pivot the jaws towards one another during a distally directed stroke of the outer tubular member so that the jaws assume a closed configuration. The cutouts or open slots are disposed alongside the jaws in the closed configuration thereof to provide clearance for tissue material grasped in and protruding laterally from the jaws.

Where the device is insertable through a working channel of a flexible endoscope, the outer tubular member preferably comprises an elongate coil and a sleeve provided at a distal end of the coil. The cutouts or slots and the fingers are provided on a distal side of the sleeve.

Pursuant to another feature of the present invention, the sleeve is provided with a longitudinal slot, closed at both a proximal end and a distal end, the slot defining a range of longitudinal motion of the sleeve and the outer tubular member. A pin fastened to the inner tubular member at least partially traverses the slot to (a) limit longitudinal motion of the outer tubular member and the sleeve relative to the inner tubular member and (b) rotationally entrain the outer tubular member to the inner tubular member.

Pursuant to a further feature of the present invention, at least one spring member is provided in contact with the jaws for biasing same towards the open configuration. The spring member may be partially located in a recess or seat provided at a distal end of a clevis to which the jaws are pivotally secured. The spring member may include a coiled portion disposed in the seat. The spring member may have opposite ends projecting from the coiled portion to engage proximal ends of the jaws. The spring member is provided in contact with the jaws for biasing same towards the open configuration.

Pursuant to yet another feature of the present invention, the device further comprises a staple disposed between the jaws. The staple has notches, recesses or apertures for receiving and securing a backbone locking element. The backbone is preferably made of rigid material and has a pair of legs slidable over a backside of the staple and securable firmly over the staple to hold the same in a closed configuration. The legs of the backbone have inwardly extending protrusions engageable in respective ones of the notches, recesses or apertures for locking the legs into place over the staple.

The staple may be provided along its backside with channels for guiding the legs of the backbone along the staple so that the protrusions are received in the notches, recesses, or apertures. A push bar is provided inside the inner tubular member, the push bar operatively engageable with the backbone for pushing the backbone onto the staple.

The distal ends of the jaws are preferably pointed for enabling the jaws to enter targeted tissue, the jaws being provided along mutually facing surfaces with grooves for seating a staple and allowing for a backbone to slide over the closed staple.

The device defined in claim 1 wherein the jaws are attached to a drive mechanism that opens and closes the jaws, the drive mechanism being attached to a handle mechanism.

BRIEF DESCRIPTION OF THE DRAWINGS

A complete understanding of the present invention may be obtained by reference to the accompanying drawings, when considered in conjunction with the subsequent, detailed description, in which:

FIG. 9 is a schematic perspective view showing the staple and backbone deployed into tissue and released from stapler.

FIGS. 10A-10E are partially schematic side elevational views of a proximal end and partially schematic cross-sectional views of a distal end of an endoscopic stapling device in accordance with the present invention, showing successive steps in the utilization of the device.

FIG. 11 is a schematic perspective view showing a staple tray assembly in accordance with the present invention.

For purposes of clarity and brevity, like elements and components will bear the same designations and numbering throughout the drawing figures.

DEFINITIONS

The term "endoscopic" is used herein to designate any of a variety of minimally invasive surgical procedures wherein optical elements are used to view internal spaces and tissues of the patient through relatively small, natural or surgically created openings in a patient. Concomitantly, the term "endoscope" as used herein refers to any optical instrument inserted through such a small opening for purposes of enabling visualization of internal tissues during a minimally invasive procedure.

An endoscopic stapling device as described herein is inserted through a working channel of an endoscopic instrument. An "endoscopic instrument" may include optical illumination and image transmission components or may be a simple tube, such as a cannula. More generally, an endoscopic instrument may be any instrument that is used to perform an endoscopic diagnostic or surgical procedure.

The term "open position angle" refers herein to the most open configuration of a staple or a pair of jaws. Two relatively inclined elements (legs, prongs, jaws) subtending a larger open position angle than another two relatively inclined elements means that the first two elements naturally open to a wider extent than the second two elements.

The term "backbone" as used herein denotes a locking element that is engageable with a staple or clip to hold the staple or clip in a closed configuration in the tissues of a patient. The term "backbone" is more particularly meant to designate a locking element that fits along the back or outside of a spring-biased staple to provide rigidity and stability to the staple in a closed configuration. Preferably, a staple used with a backbone as described herein is spring biased by internal stresses of its memory or shape alloy material to an open configuration. The backbone counteracts that spring bias to hold the staple closed upon deployment in organic tissues. In a specific embodiment disclosed herein, a staple backbone comprises a pair of legs pr prongs projecting in parallel to one another, the legs or prongs being provided with inwardly extending protrusions for mating with similarly shaped notches or recesses in respective staple legs to secure the backbone to the staple. The staple in addition or alternatively may be provided along outer surfaces of its own legs or prongs with grooves that receive the legs or prongs of the backbone in a seating relationship.

The term "active stapler components" refers herein generally to movable components of an endoscopic stapling device, which move during use of the device to effect various steps in an endoscopic stapling procedure. Those steps include, but are not necessarily limited to, ejection of a staple holder, the opening and closing of staple holder jaws, the insertion of a staple holder and an entrained staple into internal organic tissues of a patient, the movement of a backbone over a staple, the removal of staple jaws from a deployed and locked staple.

DETAILED DESCRIPTION

Figure 1:
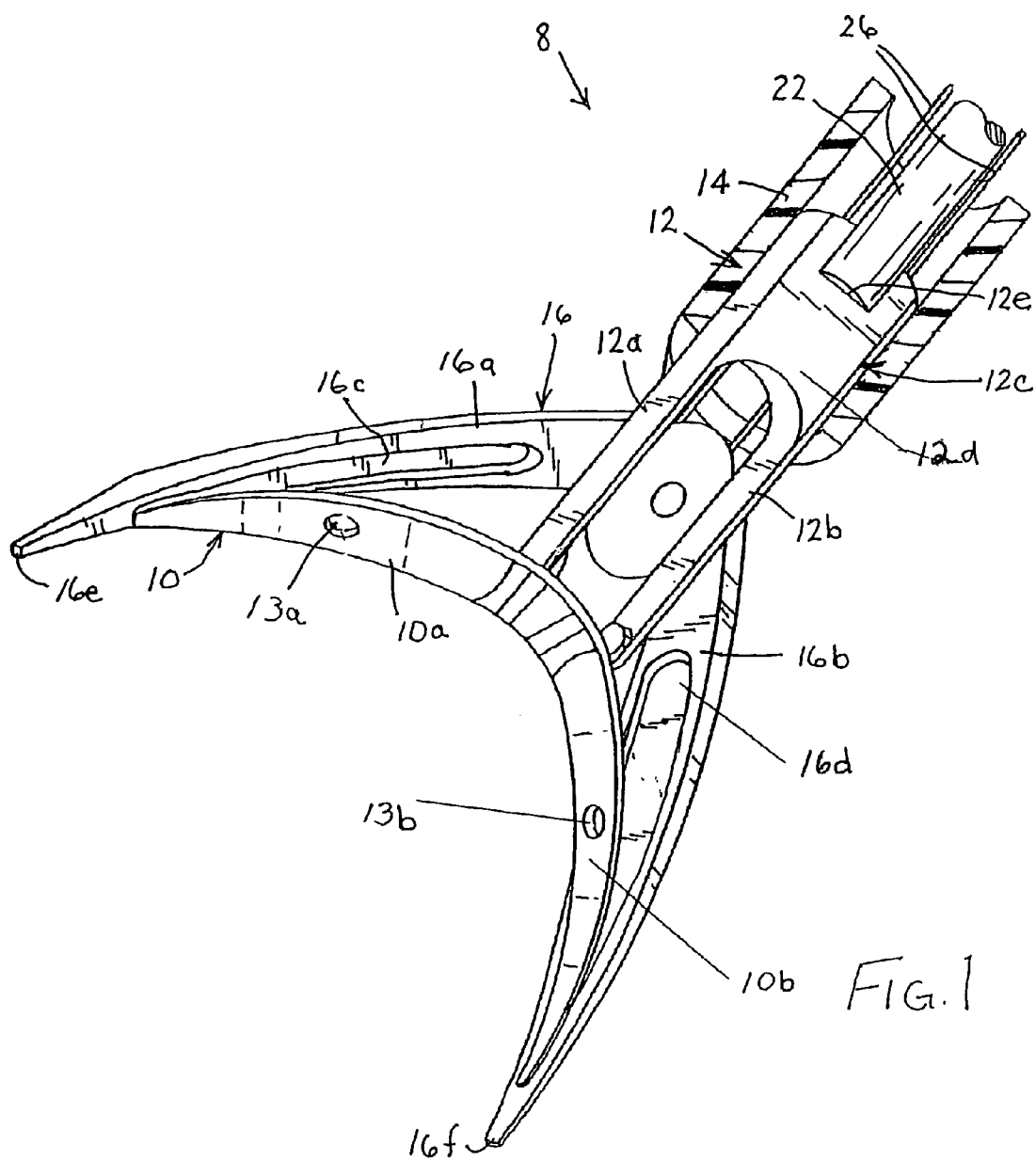
FIG. 1 is a schematic perspective view, of a cross-section of an endoscopic stapling device in accordance with the present invention, showing a staple, a backbone, and a staple holder mechanism, in an open position.

FIG. 1 is a perspective view, partly in cross section, of a distal end of an endoscopic stapling device or assembly 8 for use in inserting a staple 10 deeply into internal organic tissues of a patient. Staple 10 includes a pair of legs or prongs 10a and 10b each provided with a staple notch, aperture, or recess 13 for enabling a locking of the staple in a closed post-firing configuration. Staple 10 is locked in the closed configuration by a backbone 12 (see FIGS. 2-5) comprising a pair of legs or prongs 12a and 12b projecting parallel to one another from a body portion 12c. Body portion 12c has opposing planar faces 12d and is provided at a rear or proximal end with a cutout 12e serving as a seat for the distal end of a push bar 22. As discussed below, backbone 12 is disposed back behind the staple 10 until the staple is inserted into the tissues and is ready to be locked.

In addition to staple 10, backbone 12 and pushbar 22, endoscopic stapling assembly 8 includes a staple holder 16, an elongate tube 14, and one or more drive wires or rods 26. Staple 10 initially sits within the jaws 16a and 16b of the staple holder 16 with the backbone 12 positioned at a proximal end of the staple 10 and contained within the staple holder 16 and elongate tube 14.

Jaws 16a and 16b of staple holder 16 are formed along inner surfaces (not labeled) with respective longitudinally extending grooves or recesses 16c and 16d for removably receiving legs 10a and 10b of staple 10. Grooves 16c and 16d may be approximately the same size and shape as staple legs 10a and 10b, for seating the staple so as to prevent a forward or lateral displacement of the staple from the staple holder 16 prior to completion of a staple closing operation.

Staple 10 is biased to an open position angle greater than the open position angle of staple holder 16, thus exerting outward pressure on staple holder 16 and serving to maintain staple 10 within staple holder 16 in an open configuration of the staple and the staple holder. This force contributes to staple retention and maintaining staple 10 in position inside the staple holder 16 when staple 10 and staple holder 16 are inserted into the targeted tissue to be secured. Backbone 12 contributes to staple 10 maintaining the preferred position inside staple holder 16 jaws by providing resistance against staple 10 and keeping staple 10 from sliding proximally as these components are inserted into tissue. Staple holder 16 is connected to elongate tube 14 and an actuation assembly, which includes drive wires or rods 26 that activate the jaws 16a and 16b of the staple holder 16. Elongate tube 14 contains push bar 22 which slides distally to push backbone 12 over staple 10 after the staple and the holder 16 have been inserted into tissues, as discussed below with reference to FIGS. 6-9. Push bar 22 is operatively connected to a component of a handle mechanism 24 (FIGS. 10A-10E) which controls the forward motion of the push bar 22.

Figure 2:
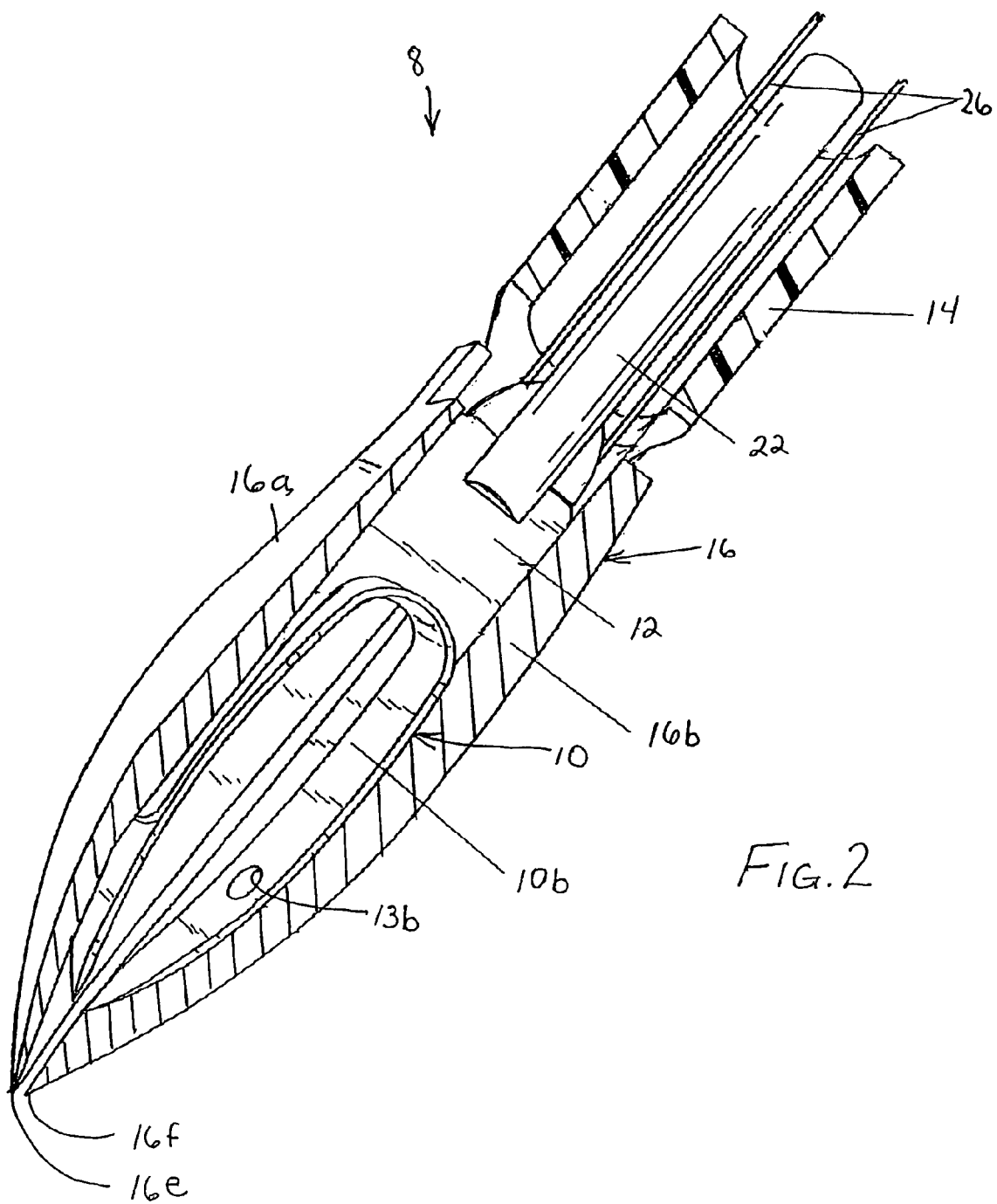
FIG. 2 is a schematic perspective view, similar to FIG. 1, showing the endoscopic stapling device of that drawing figure in a closed position.

FIG. 2 is a cross sectional view of the distal end of endoscopic stapling assembly 8, showing staple 10 with staple notches 13a and 13b in legs 10a and 10b, backbone 12 with two protrusions 15a and 15b extending inwardly from respective legs or prongs 12a and 12b, staple holder 16, elongate tube 14, drive wires 26, and push bar 22, with staple 10 and holder 16 disposed in a closed position. After the insertion of holder 16 and staple 10 into target tissues inside a patient, backbone 12 is slid forward over the closed staple 10 and locked into position by means of staple notches 13a and 13b and backbone protrusions 15a and 15b. Staple holder 16 is made from a rigid metal with opposing jaws that meet and align when closed. The closing of staple holder 16 jaws results in the closing of staple 10 and alignment of staple legs 10a and 10b.

Figure 3:
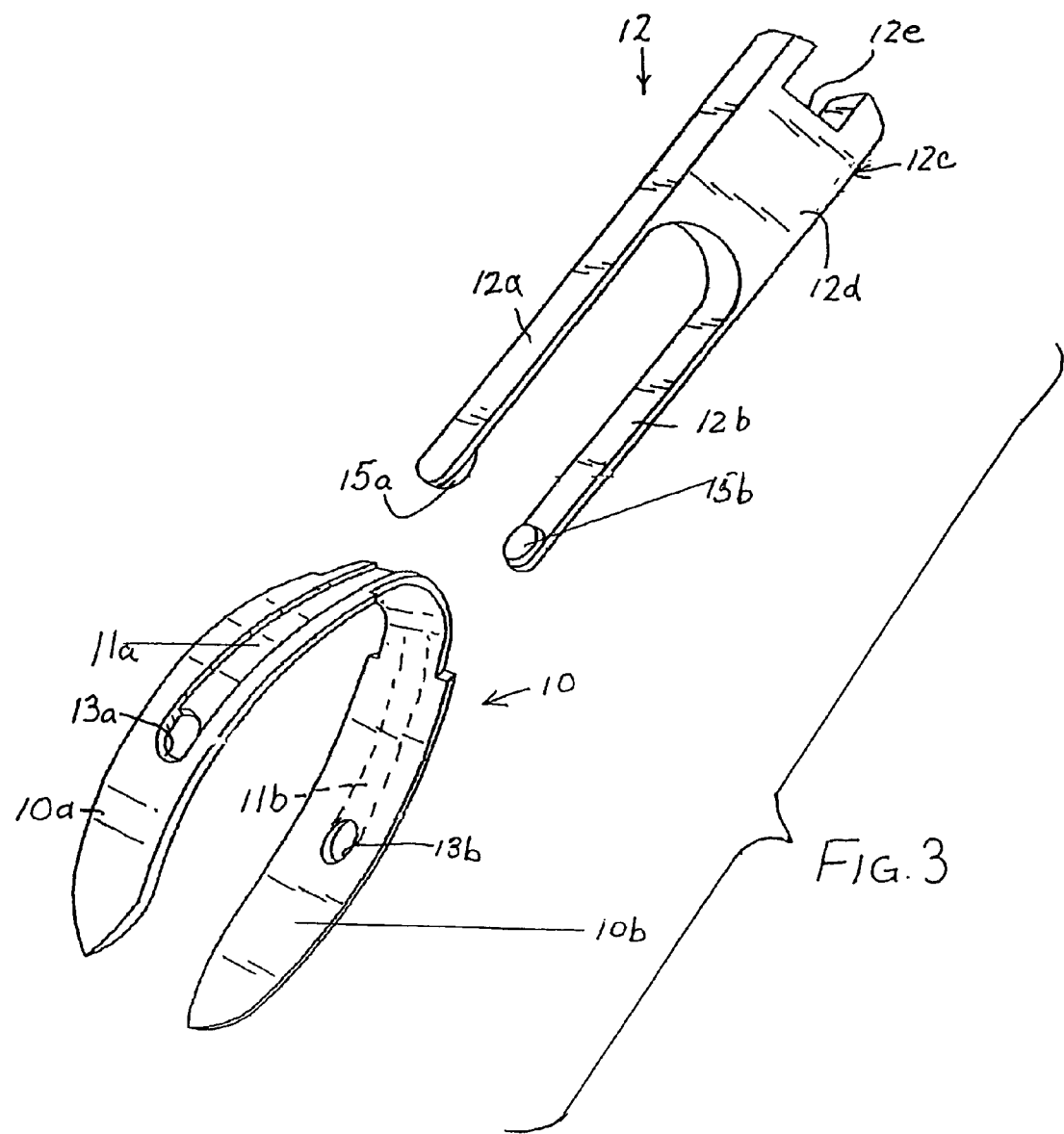
FIG. 3 is an exploded schematic perspective view showing the staple and the backbone of FIGS. 1 and 2.

FIG. 3 is a perspective view of staple 10 which is composed of a flexible metal that allows for repeat opening and closing of staple 10. Legs 10a and 10b of staple 10 are joined at the proximal end or formed by bending or folding a single metal component at a center point. Staple legs 10a and 10b have preformed channels 11a and 11b on the outside surfaces of the legs. Notches 13a and 13b communicate with the respective channels or grooves 11a and 11b. Channels 11a and 11b serve to guide legs 12a and 12b of backbone 12 over legs 10a and 10b of staple 10 during a distally directed staple-closing stroke of push bar 22, while notches 13a and 13b serve to guide and secure the backbone 12 and, more specifically, backbone protrusions 15a and 15b when backbone 12 is slid over the closed staple 10 in the target organic tissues. Backbone 12 is composed of rigid metal whose structural force is greater than the open angle force of staple 10. Channels 11a and 11b may be opposite end portions of a single channel or groove in the backside or outwardly facing surface (not separately labeled) of staple 10.

Figure 4:
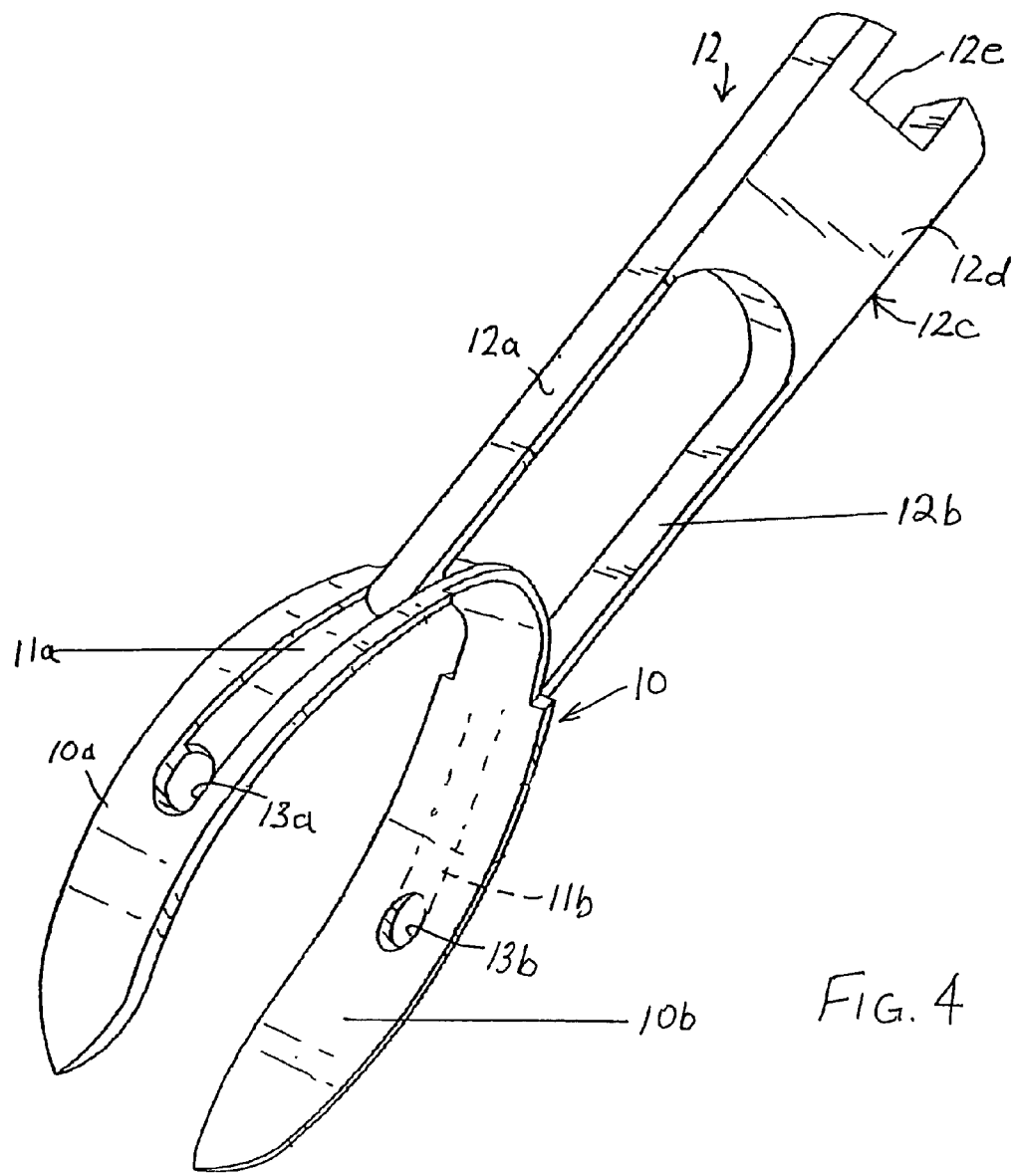
FIG. 4 is a schematic perspective view similar to FIG. 3, showing the staple in an open position with the backbone in a proximal position.

FIG. 4 is a perspective view of staple 10 and backbone 12 in proximal position to staple 10. The configuration of FIG. 4 occurs when staple holder 16 and staple 10 are partially opened after insertion of the distal end portion of assembly 8 into a patient during an endoscopic or laparoscopic surgical procedure.

Figure 5:
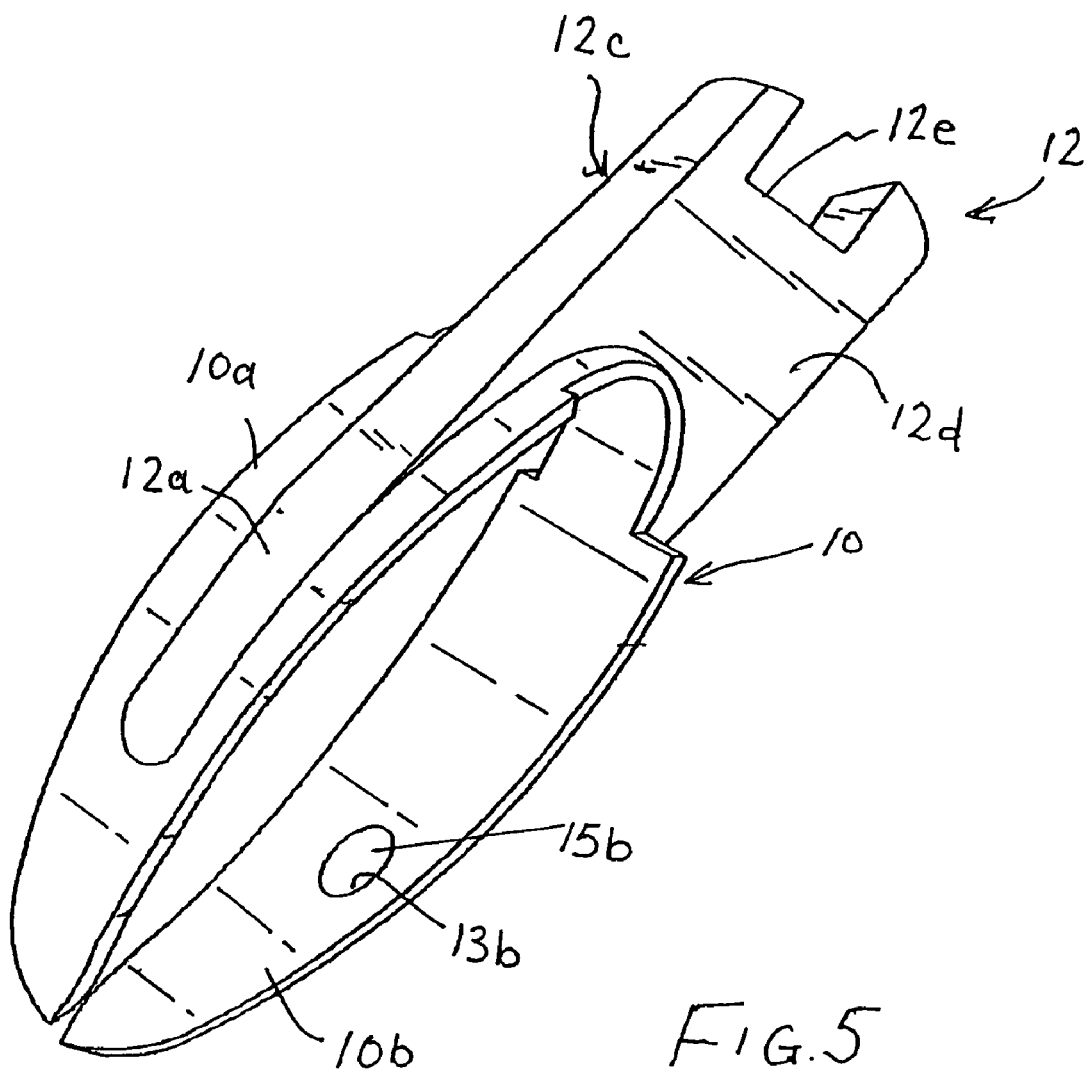
FIG. 5 is a schematic perspective view showing the staple of FIGS. 3 and 4 in a closed position with the backbone disposed over the staple, locking the staple in the closed position.

FIG. 5 is a perspective view of the backbone 12 with legs or prongs 12a and 12b disposed in the staple closed position over respective legs 10a and 10b of staple 10. Backbone 12 is slid from the proximal end of staple 10 toward the distal end of staple 10 along the preformed channels 11a and 11b in the outer walls of staple 10. Backbone protrusions 15a and 15b have diameters that match the diameters of channels 11a and 11b and of notches 13a and 13b formed in the outside surfaces or faces of staple 10. Backbone protrusions 15a and 15b lock into the respective notches 13a and 13b when backbone 12 is fully pushed down channels 11a and 11b of staple 10 in the closed position. Backbone 12 locks in place, maintaining staple 10 in a fully closed position over the captured tissue.

Figure 6:
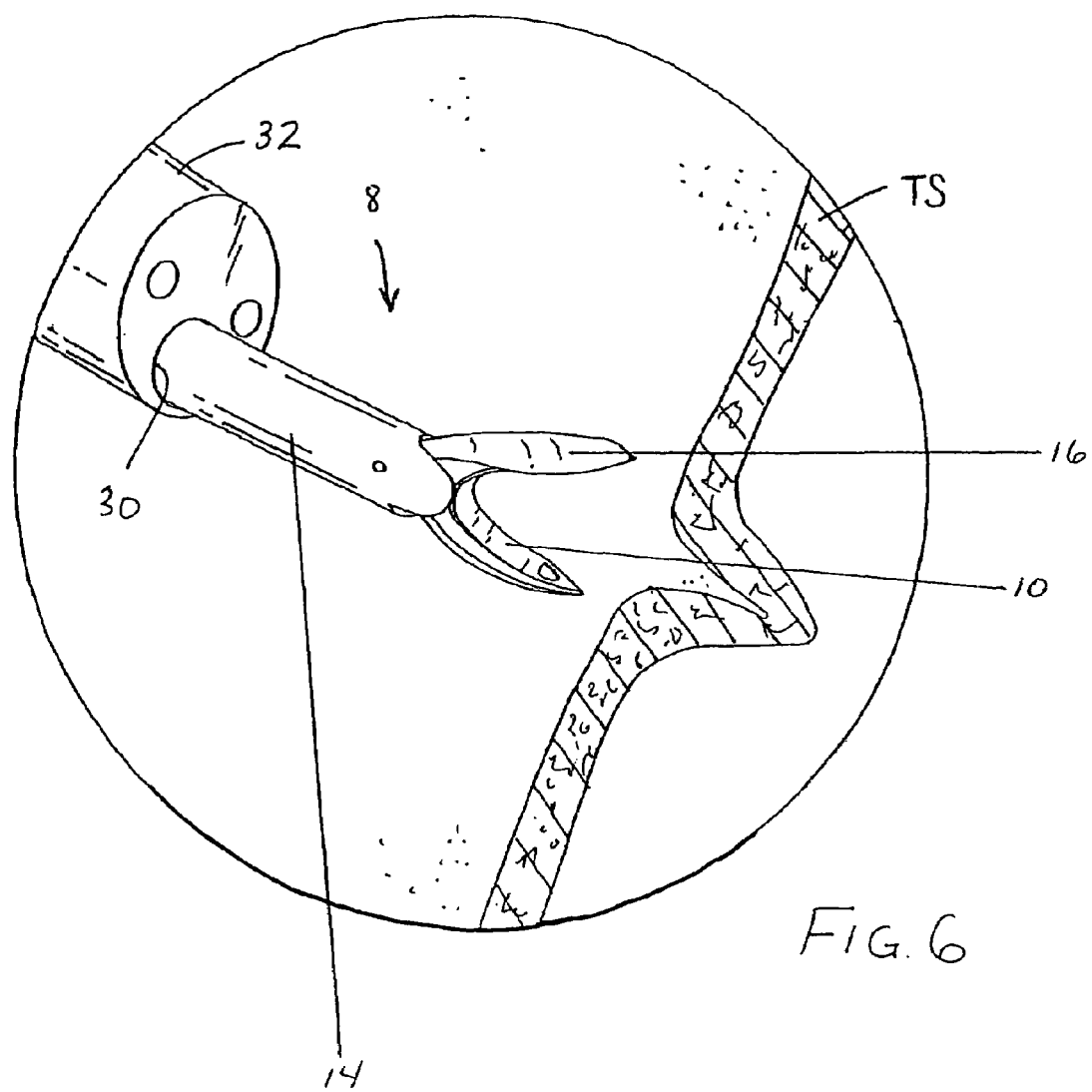
FIG. 6 is a schematic perspective view showing the staple and stapler device of FIGS. 1 and 2 approaching tissue to be secured

FIG. 6 is a perspective view of the distal end of endoscopic stapling device or assembly 8 as the device is passed through a working channel 30 of an endoscope 32 and approaches target tissue TS. Staple holder 16 is opened by manipulation of handle 24 (FIGS. 10A-10E) after the holder emerges from the distal end of the endoscope 32. In the opened configuration of holder 16 shown in FIG. 7, the staple 10 and the backbone 12 have the configurations and relative positions shown in FIG. 4.

It is to be noted that staple holder 16 has a pointed distal end for penetrating the targeted tissue. More particularly, holder jaws 16a and 16b have pointed tips 16e and 16f that enable a deep penetration of jaws 16a, 16b and concomitantly staple 10 into the target tissue TS.

Figure 7:
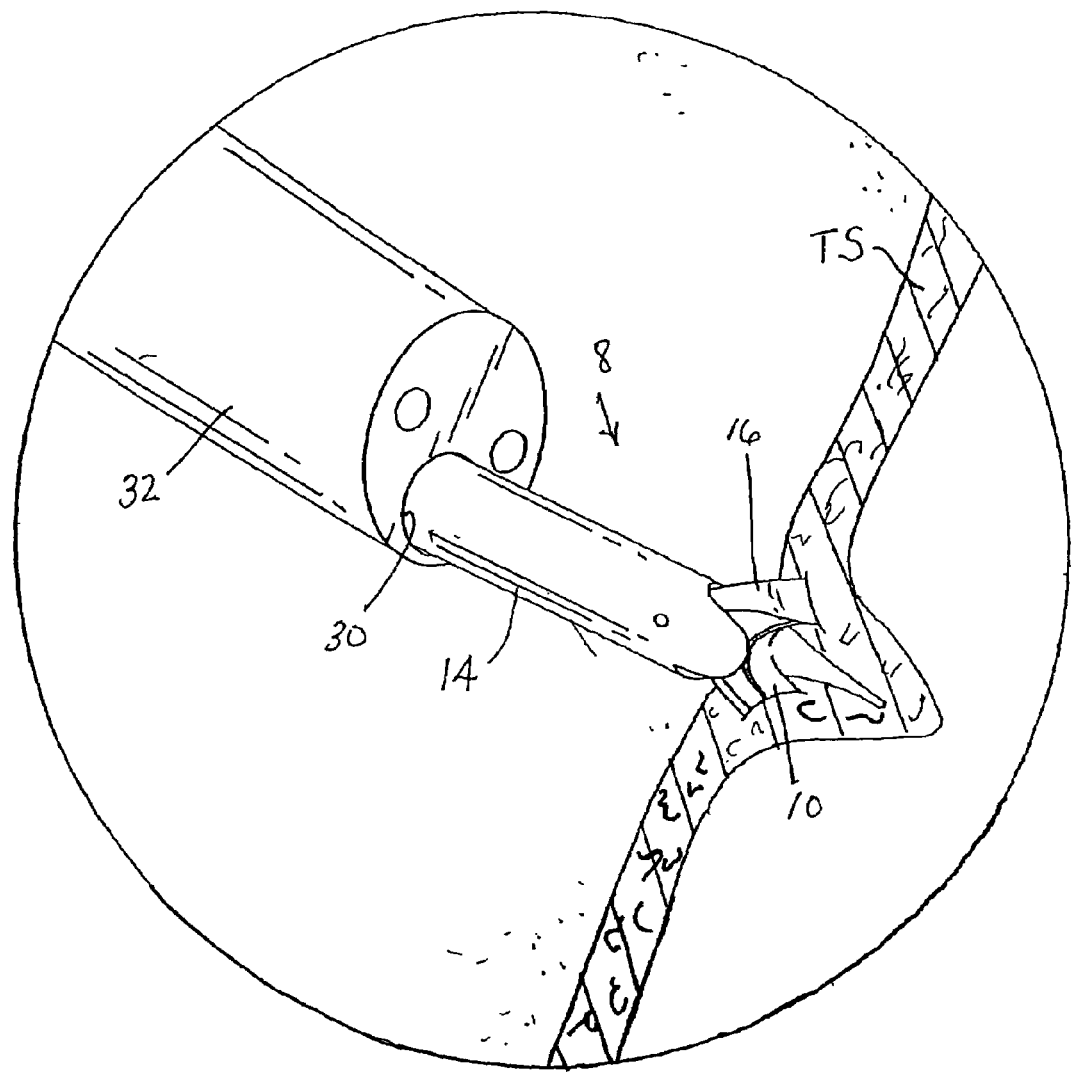
FIG. 7 is a schematic perspective view showing the staple and stapler device inserted into tissue to be secured

FIG. 7 is a perspective view of the distal end of endoscopic stapling device 8 as the jaws 16a and 16b, together with staple 10, penetrate the targeted tissue TS. When the tissue TS is located by the endoscopist, staple holder 16, in the open position, is pushed into the tissue. Staple 10 and backbone 12 still have the configurations and relative positions of FIG. 4.

Figure 8:
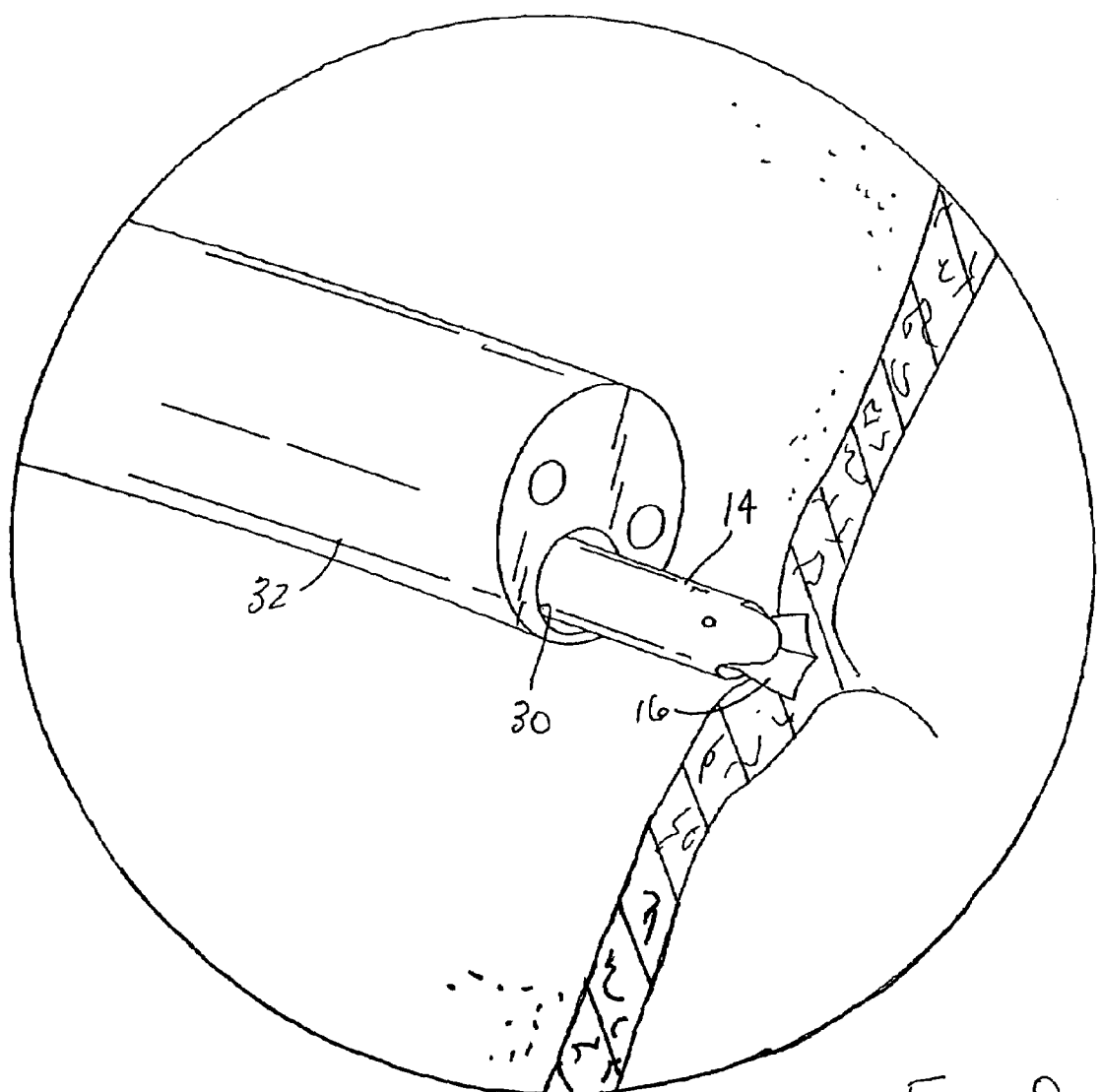
FIG. 8 is a schematic perspective view showing the staple and stapler in closed position securing tissue
Figure 12:
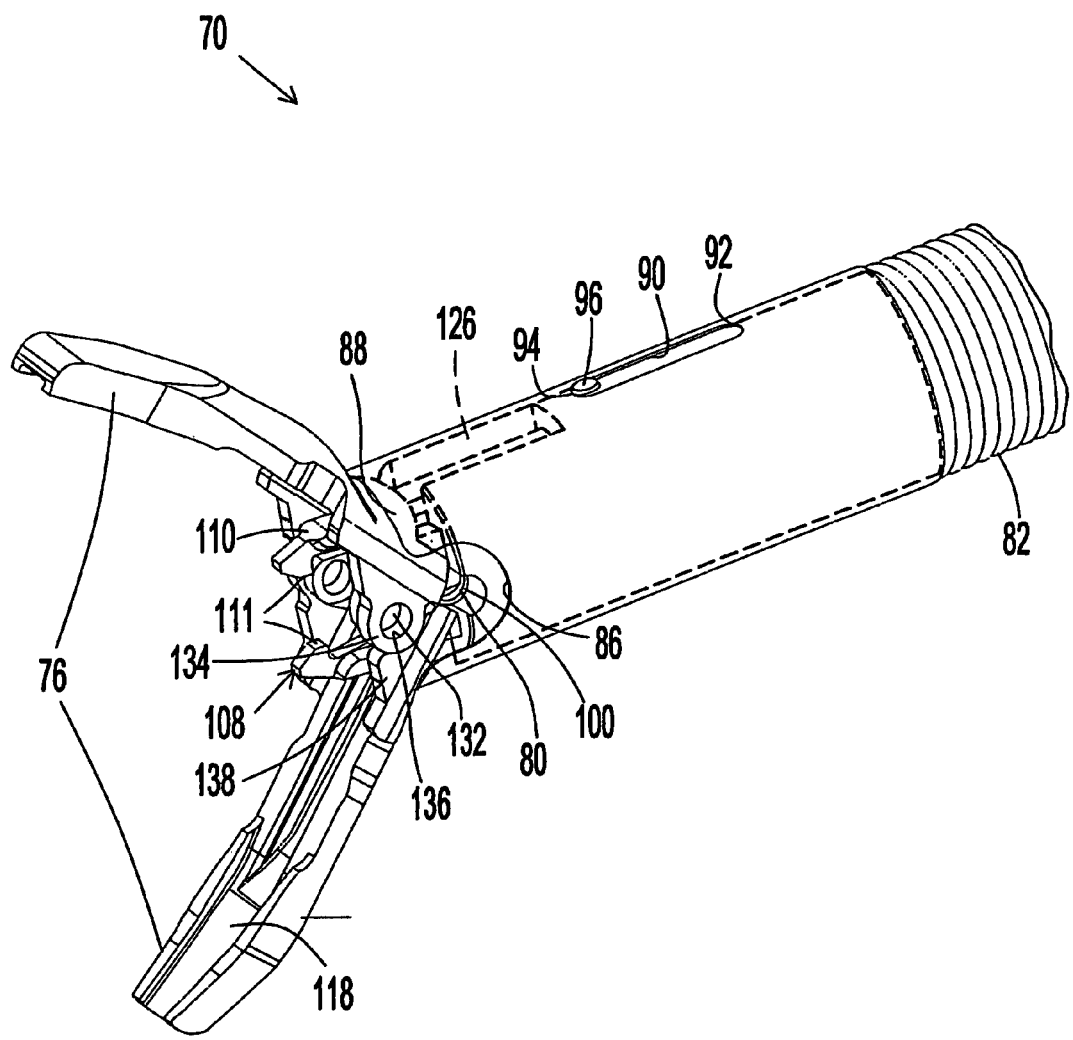
FIG. 12 is a perspective view of a distal end portion of another endoscopic clip or staple applicator in accordance with the present invention, with staple-holding jaws in an open configuration.

FIG. 8 is a perspective view of the distal end of the endoscopic stapling device 8 as the staple holder 16 is closed over the captured tissue TS. The closure of holder 16 causes staple 10 to close as well. Staple holder 16 is closed by manipulation of the device handle 24, capturing the targeted tissue TS. More specifically, this closure may be effectuated, for instance, by drawing wires or rods 26 in a proximal direction. Handle 24 is then manipulated in a second movement, which shifts the push bar 22 in the distal direction and consequently advances the backbone 12 over the closed staple 10 that is inside the staple holder 16. Backbone 12 locks in place on the closed staple 10, as discussed above with references to FIGS. 2 and 5, and secures the captured tissue TS. Staple holder 16 is then opened by a reverse manipulation of the handle 24 and removed from the tissue. Staple 10 and backbone 12 remain on the captured tissue.

Figure 9:
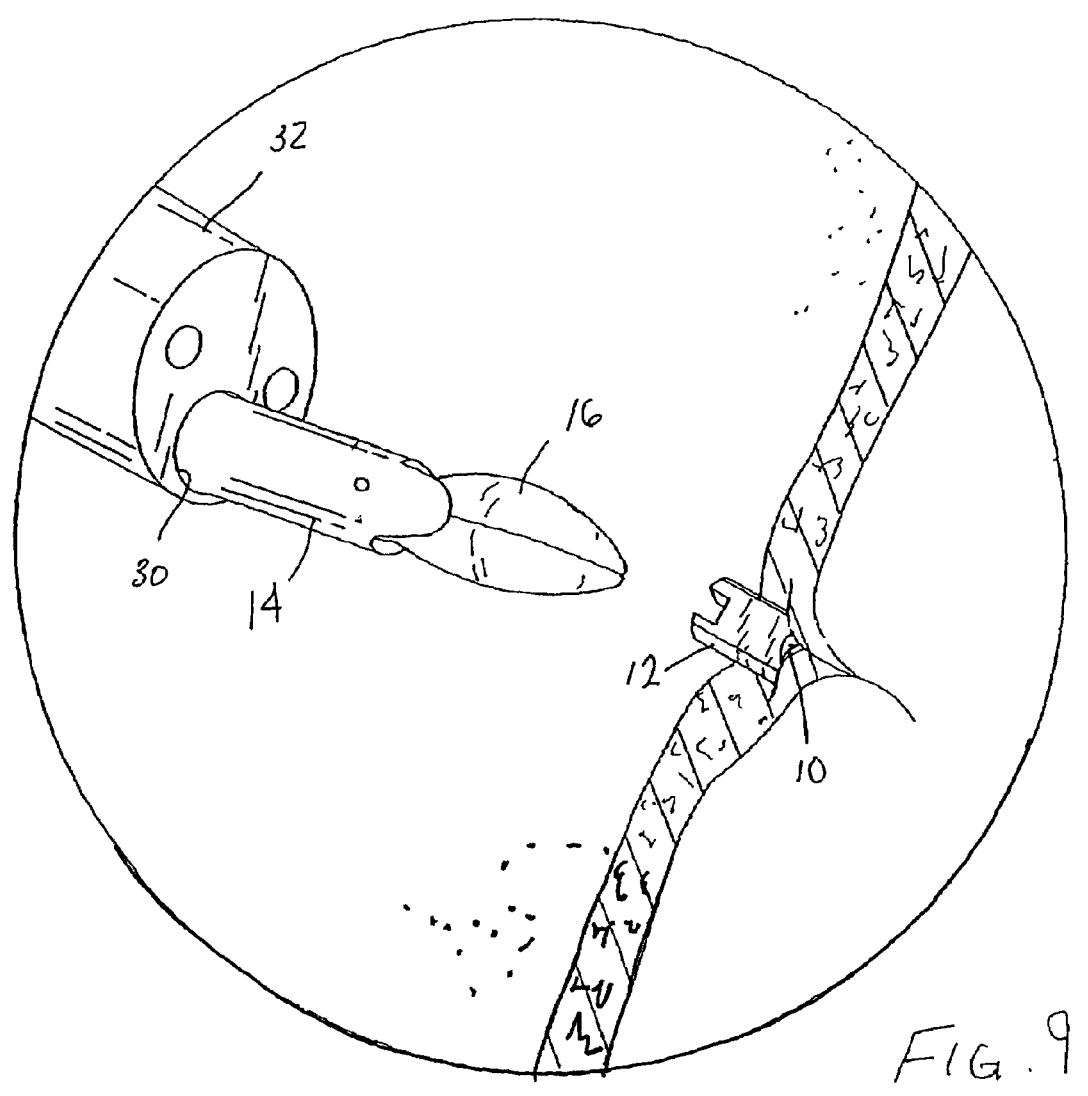

FIG. 9 is a perspective view of the distal end of the endoscopic stapling device 8 after deployment of staple 10 and backbone 12. Staple holder 16 is closed by manipulation of handle 24 and pulled back through the endoscope working channel 30.

FIGS. 10A-10E are partially schematic elevational views of the handle mechanism 24 at a proximal end of an endoscopic stapling device 34. FIGS. 10A-10E are also partially schematic cross-sectional views of a stapling mechanism 36 at a distal end of the endoscopic stapling device 34. FIGS. 10A-10E shows successive steps in the utilization of the device.

As shown in FIGS. 10A-10E, stapling device 34 includes elongate tube 38 fixed at a proximal end to handle mechanism 24. A staple holder 40 similar to staple holder 16 is connected to elongate tube 38 and an actuation assembly which includes a drive wire or rod 42 that activates jaws 40a and 40b of the staple holder 40. This actuation mechanism is connected at its proximal end to handle mechanism 24.

Handle mechanism 24 is composed of formed plastic or metal components that slide within each other. One set of components 44 controls the opening and closing of the staple holder jaws 40a and 40b another set of components 46 controls the sliding of a push bar 48 that advances a backbone 50 over a staple 52 once the staple has been inserted and closed in target tissue. Backbone 50 and staple 52 have interacting locking structures as described above particularly with references to FIGS. 3-5.

Drive wire or rod 42 effectuates the closing of jaws 40a and 40. Like jaws 16a and 16b, jaws 40a and 40b may be provided with a biasing spring (not shown) tending to open the jaws upon an ejection thereof into a body cavity. Alternatively, drive wire or rod 42 may be used to both open and close the jaws 40a and 40b in response to distal and proximal movement of actuation component 44 under the direct control of the operator. Jaws 40a and 40b may be connected to another tube (not shown) internal to tube 38.

FIG. 10A shows staple 52 and staple holder 40 disposed within the distal end of tube 38 prior to ejection therefrom during an endoscopic or laparoscopic stapling procedure. FIG. 10B shows staple 52 and staple holder 40 opened by a controlled distal movement of actuation components 44 and 46 (arrows 45 and 47 in FIGS. 10A and 10B). Staple 52 is now opened with backbone 50 disposed proximally thereof, as discussed above with reference to FIG. 4. After an insertion of the opened staple holder 40 and staple 52 into a desired tissue site (see FIGS. 7 and 8), actuation component 44 is manipulated to close jaws 40a and 40b and actuation component 46 is pushed in the distal direction, as indicated by an arrow 54 to cause push bar 48 to advance backbone 50 over staple 50 (FIGS. 10C and 10D), as discussed above with reference to FIGS. 5 and 8. After the locking of staple 52 by backbone 50, actuation components 44 and 46 are moved in opposing directions, as indicated by arrows 56 and 58 in FIG. 10E, to eject backbone 50 and close jaws 40a and 40b.

FIG. 11 is a perspective view of a staple tray 18, which is a formed holder that contains additional staples 10 (or 52) and backbones 60 and facilitates in the reloading of staple holder 16 (or 40). Staple tray 18 has a base 62 formed with a series of holes or slots 64, which accept the distal tips of staples 10 in the open configuration thereof. A second level 68 of staple tray 18 is positioned securely over the base 62 of the staple tray 18 and has a series of aligned holes 66 that securely hold backbones 60 in proximal contact to staples 10. The second tray level 68 thus serves as an orientation structure for maintaining a plurality of backbones 60 at proximal ends of the staples 10 in the base 62 of the tray 18. When reloading staple holder 16, the staple holder is placed at the proximal end of backbone 60, push bar 22 (or 48) is retracted and staple holder 16 is slid over staple 10 capturing staple 10 in the opposing slots 16c, 16d on the inside surfaces of the staple holder jaws 16a and 16b.

Figure 17:
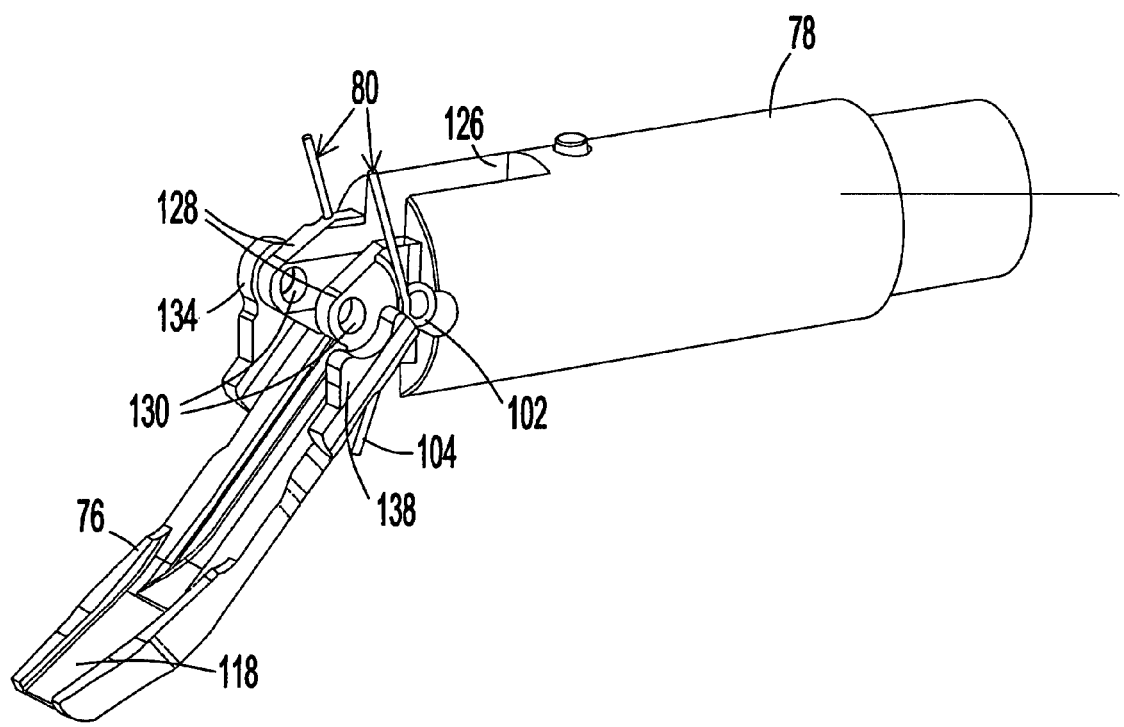
FIG. 17 is a partial perspective view, partially broken away, of the distal end portion of the endoscopic clip or staple applicator of FIGS. 12-16, showing the biasing springs of FIG. 16.
Figure 18:
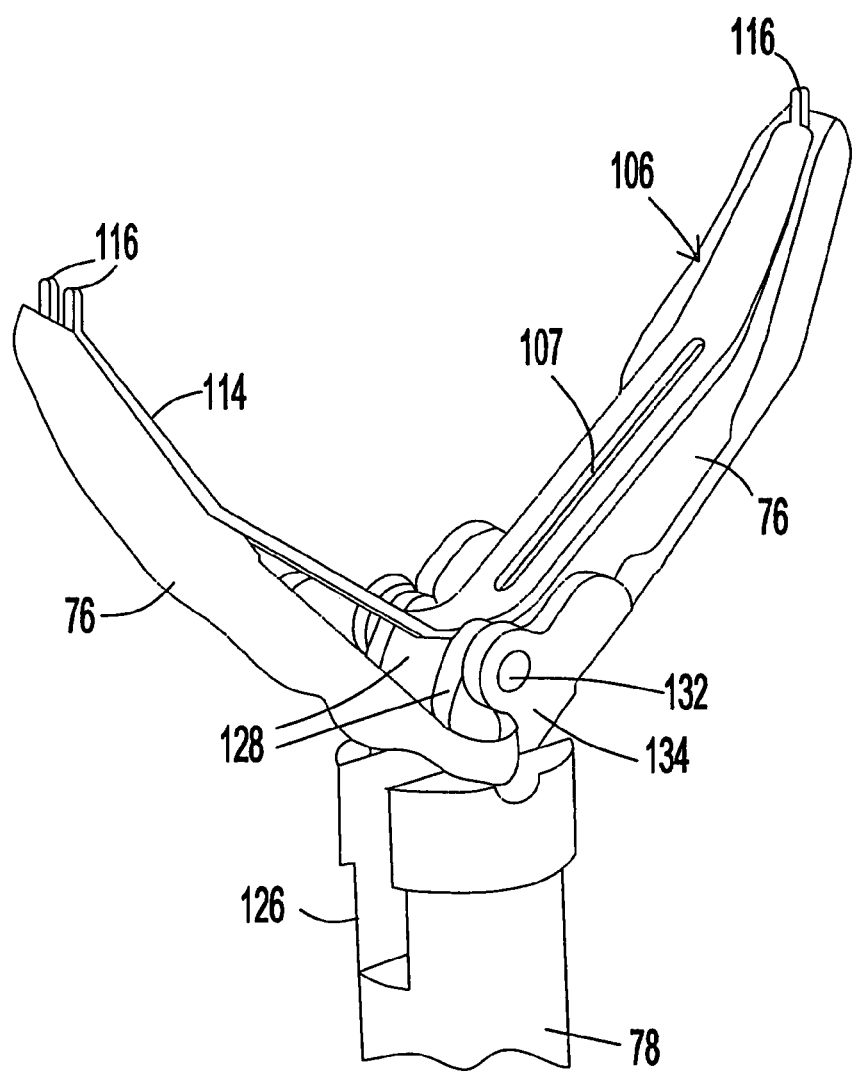
FIG. 18 is a partial perspective view of the partial perspective view of the endoscopic clip or staple applicator of FIGS. 12-17, showing a staple inserted between the open jaws.
Figure 19:
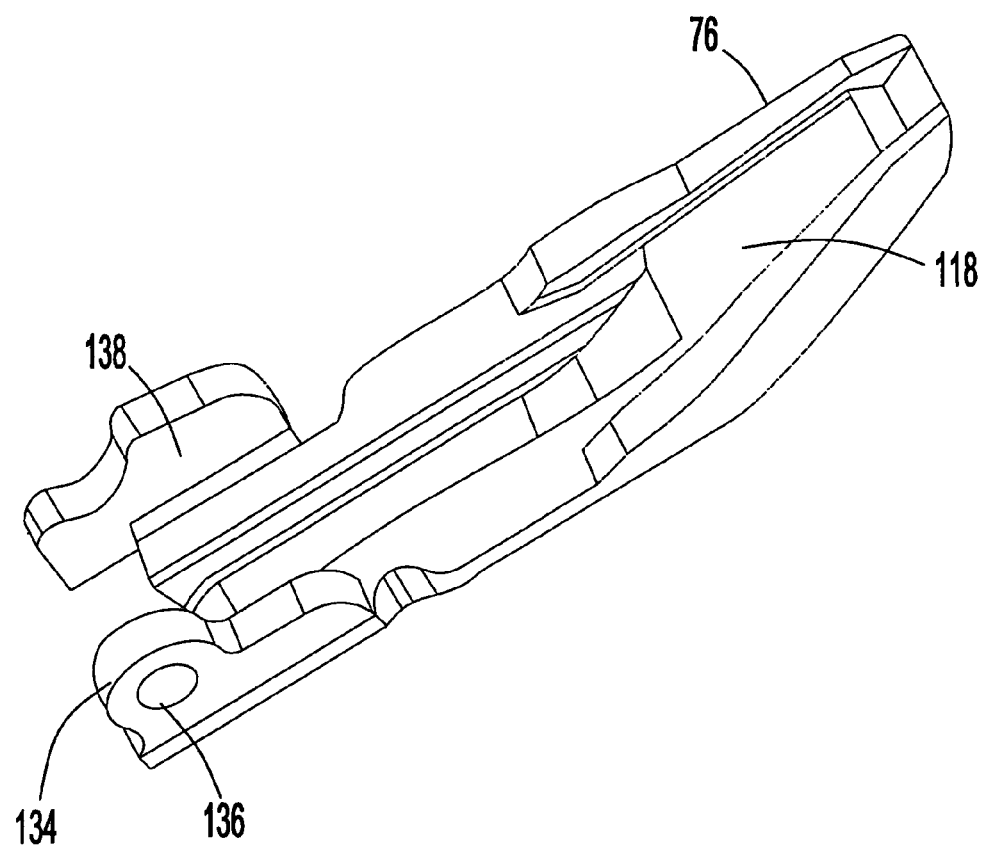
FIG. 19 is a perspective view of one of the jaws shown in FIGS. 12-18.

As illustrated in FIGS. 12-19, a modified endoscopic clip or staple applicator 70 comprises an actuator handle 72 (FIG. 13A) and an elongate flexible inner tubular member 74 (FIGS. 13 and 14) in the form of a coiled wire operatively connected at a proximal end to the handle. Two identical jaws 76, shown in isolation in FIG. 19, are pivotably mounted to a distal end of inner tubular member 74 and particularly to a clevis 78 forming a distal end member of the inner tubular member.

Figure 13:
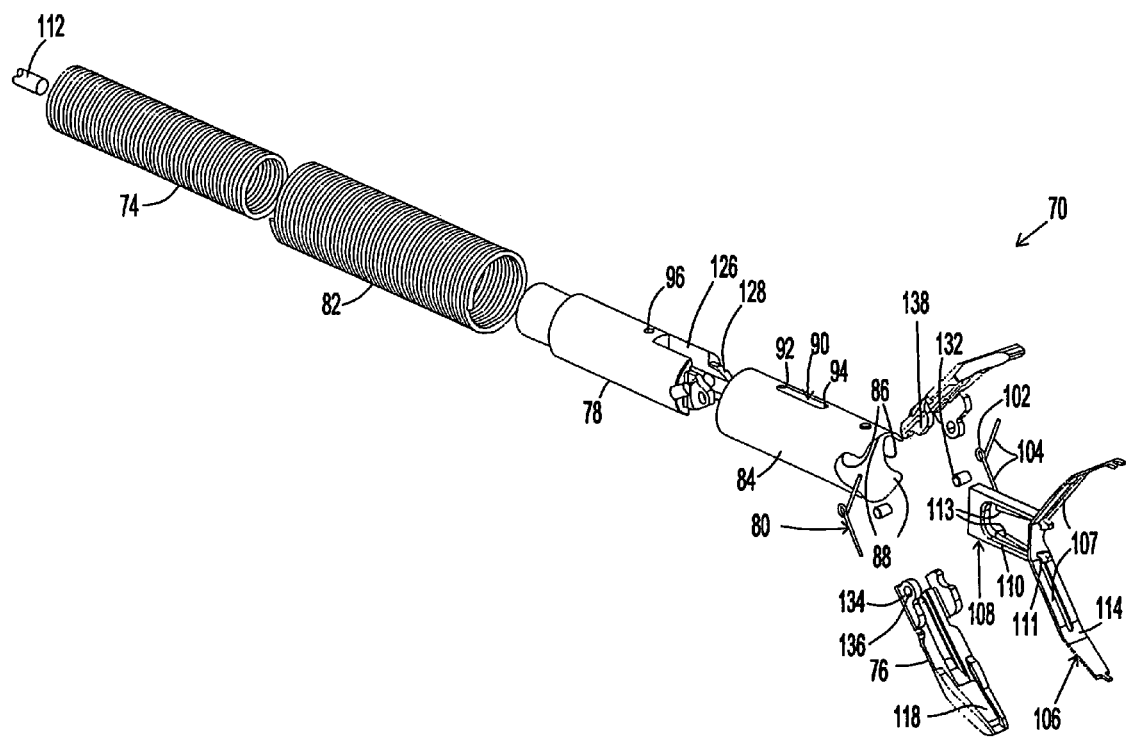
FIG. 13 is an exploded perspective view of the endoscopic clip or staple applicator of FIG. 12.
Figure 13A:
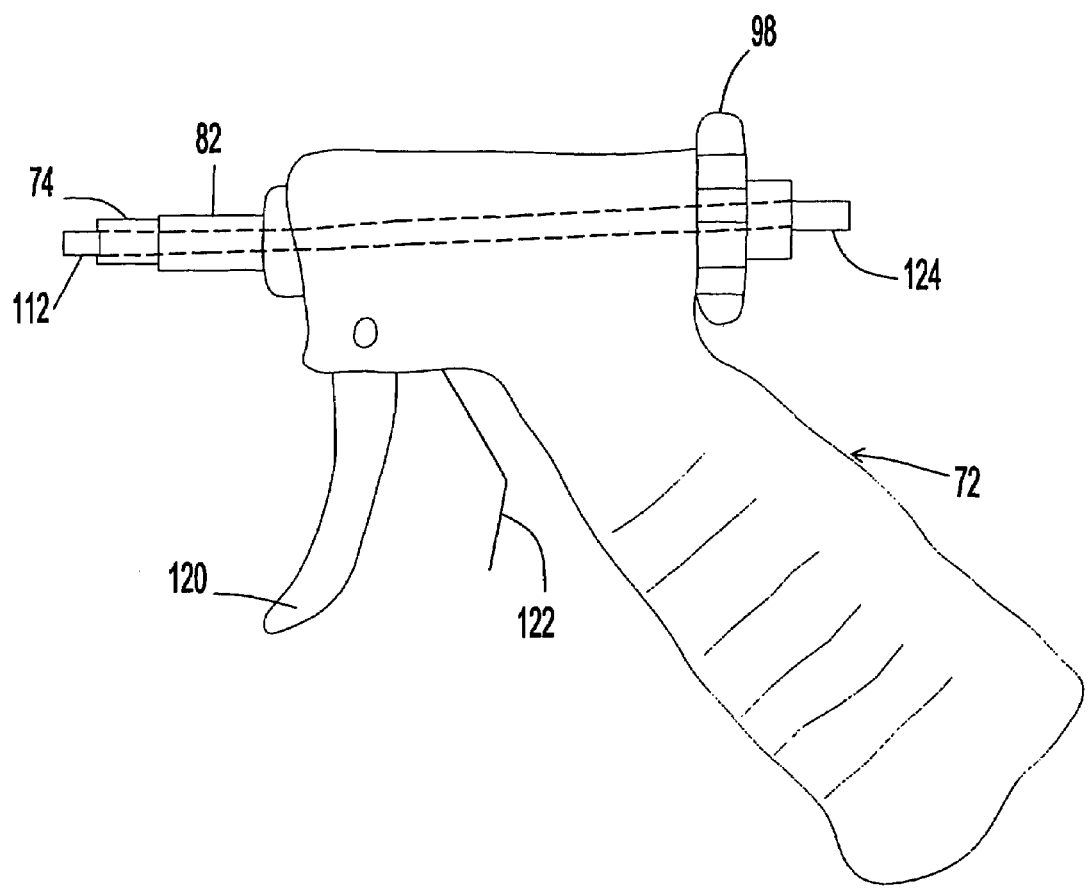
FIG. 13A is a schematic side elevational view of a handle or hand grip disposed at a proximal end of the endoscopic clip or staple applicator of FIGS. 12 and 13.

As shown in FIGS. 13, 17, and 18, clevis 78 has a distal end formed with an axial slot 126 that facilitates manufacture. In addition, clevis 78 has a pair of distally extending noses 128 provided with apertures 130 that receive respective pivot pins 132 (FIG. 13) about which jaws 76 turn. As shown in FIG. 19, jaws 76 are each provided along one side at the proximal end with a flange 134 having an aperture 136 traversed by a respective pivot pin 132. A flange 138—on an opposite side of the jaw 76 is shaped to engage and ride along flange 134 (see FIG. 12) during jaw movement.

Figure 16:
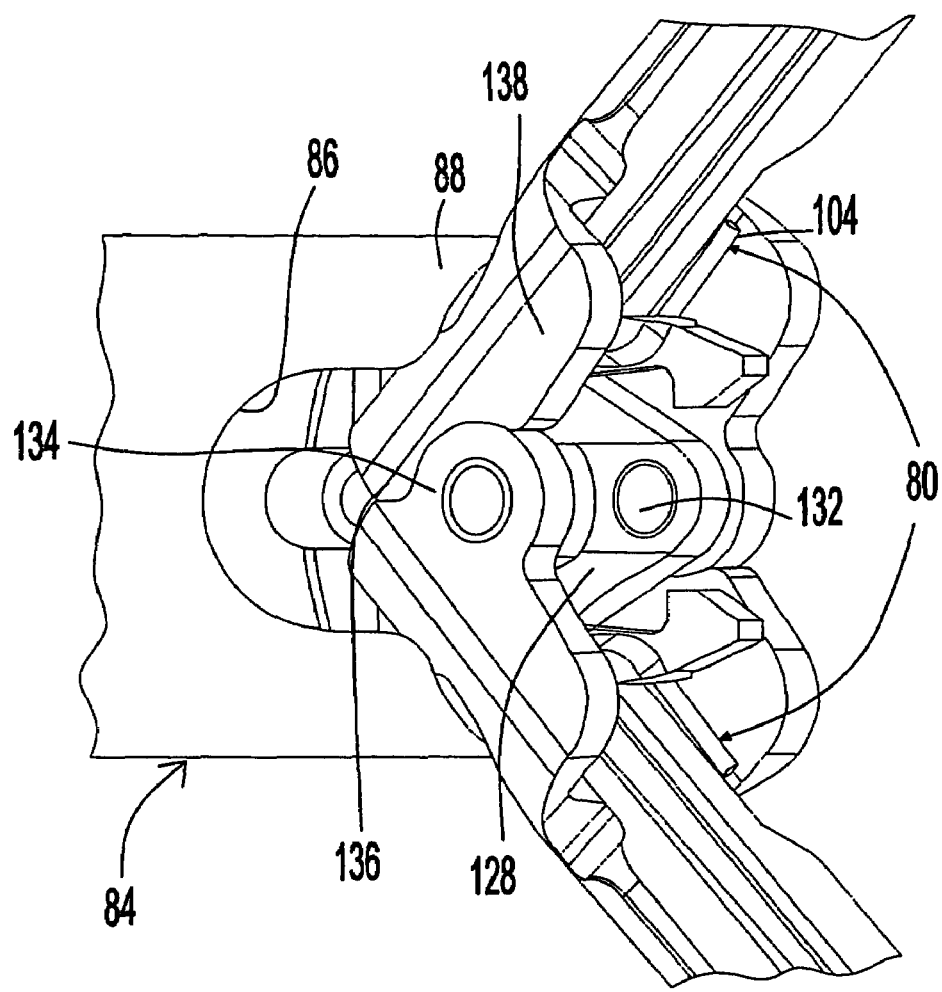
FIG. 16 is a partial perspective view of the distal end portion of the endoscopic clip or staple applicator of FIGS. 12-15, showing springs for biasing the jaws to the open configuration.

Jaws 76 are biased to an open configuration by virtue of two spring members 80 (FIGS. 13, 16, and 17). The endoscopic clip or staple applicator 70 further comprises an elongate flexible outer tubular member 82 in the form of a coiled wire provided at a distal end with a jaws-actuating sleeve 84. Outer tubular member 82 is operatively connected at a proximal end to handle 72 (FIG. 13A) and slidably surrounds inner tubular member 74.

Figure 15:
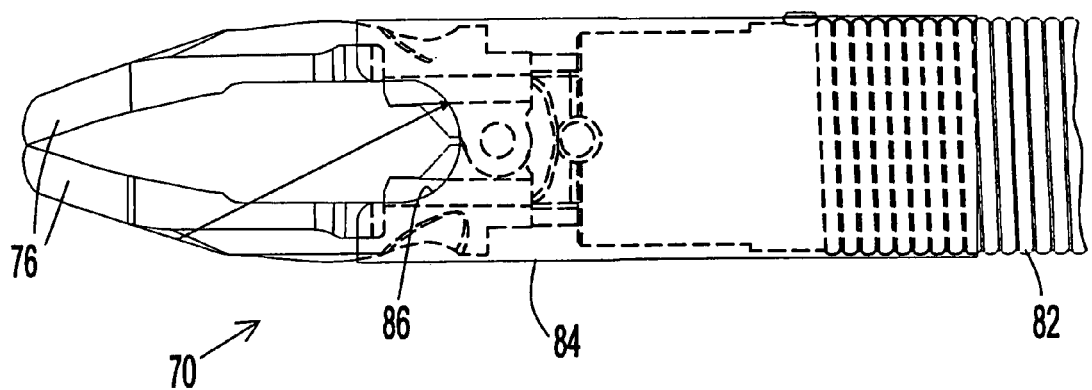
FIG. 15 is a side elevational view of the distal end portion of the endoscopic clip or staple applicator of FIGS. 12-14, showing the jaws in a closed configuration.

Outer tubular member 82, particularly actuator sleeve 84 thereof, is provided at a distal end with two cutouts or open slots 86 diametrically opposed to one another to define a pair of longitudinally extending opposed fingers 88. Fingers 88 are engageable with respective ones of the jaws 76 to pivot the jaws towards one another during a distally directed stroke of outer tubular member 82 so that the jaws assume a closed configuration (FIG. 15). Cutouts or slots 86 are disposed alongside jaws 76 in the closed configuration and thereby assure that sleeve 84 does not interfere with the target tissue during a grabbing of the tissue by jaws 76. Cutouts or slots 86 have an additional function, in that jaws 76 will not be able to close completely in some cases, if there is a large amount of tissue clamped between them. Cutouts or slots 86 allow sleeve 84 and particularly fingers 88 to flex open enough to slide over the slightly open jaws and close them. Should sleeve 84 be too rigid, i.e. no slits, the sleeve would be stopped during a distally directed closure stroke upon encountering jaws 76.

Sleeve 84 is provided with a longitudinal slot 90, closed at both a proximal end 92 and a distal end 94. Slot 90 defines a range of longitudinal motion of sleeve 84 and concomitantly outer tubular member 82. A pin 96 fastened to inner tubular member 74, and more particularly to clevis 78, at least partially traverses slot 90 to limit longitudinal motion of outer tubular member 82 and sleeve 84 relative to inner tubular member 74. In addition, pin 96 cooperates with slot 90 to rotationally entrain outer tubular member 82 to inner tubular member 74 so that when jaws 76 are rotated about a longitudinal axis by means of a thumb wheel 98 (FIG. 13A) on handle 72, sleeve 84 rotates the same amount about the same longitudinal axis. In that way, cutouts or slots 86 remain laterally disposed relative to saws 76.

Spring members 80 are partially located in respective recesses or seat grooves 100 provided at a distal end of clevis 78 (FIGS. 13, 17). As best seen in FIG. 13, spring members 80 include a coiled or substantially circular middle region 102 integral with two linear end segments 104. Middle region 102 is disposed in the respective recess or seat 100. Opposite end segments 104 project from coiled middle portion 102 to engage proximal ends of jaws 76, as shown in FIG. 16.

As shown in FIG. 18, a staple 106 is disposed between jaws 76 at the onset of a stapling operation. Staple 106 is structurally and functionally similar to staple 10 and is biased by internal spring forces to assume an open configuration. Staple 106 and springs 80 both exert a biasing force on jaws 76, forcing them to an open configuration. Opening of jaws 76 by springs 80 after deployment of staple 106 simplifies loading the device with a new staple. Springs 80 are held in position owing to recesses or grooves 100 in clevis 78 and due to the fact that the springs are partly sandwiched between the clevis and the jaws.

Figure 14:
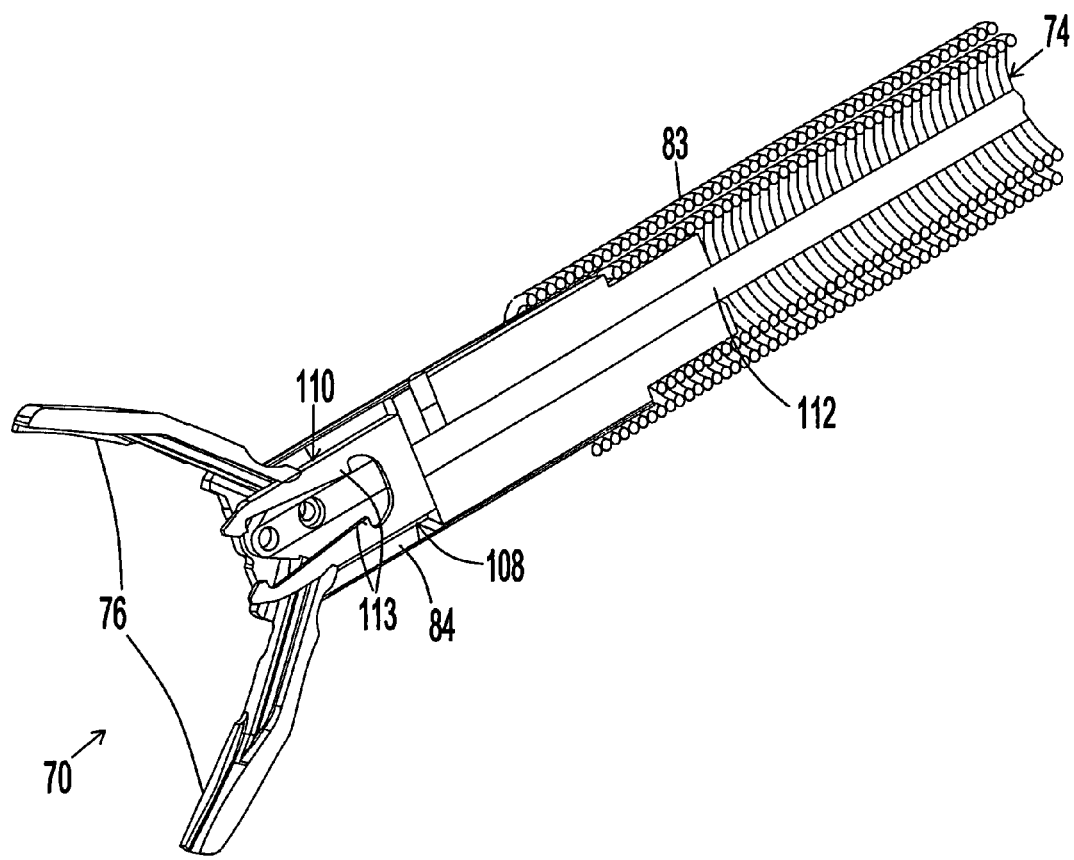
FIG. 14 is a perspective view, broken away in longitudinal cross-sectional, of the distal end portion of the endoscopic clip or staple applicator of FIGS. 12 and 13.

Staple 106 is provided with elongate notches, recesses or apertures 107 for receiving and securing a U-shaped backbone locking element 108 (FIGS. 13 and 14). Backbone 108 is structurally and functionally similar to backbone 12 and is likewise preferably made of rigid material. Backbone 108 has a pair of legs 110 slidable over a backside of staple 106 and securable firmly over the staple to hold the same in a closed configuration. At their distal ends, legs 110 of backbone 108 have inwardly extending protrusions 111 that insert into notches or apertures 107 in staple 106 for initially entraining the backbone. Legs 110 of backbone 108 are further provided with inwardly extending ribs or fins 113 that insert into notches or apertures 107 to lock backbone 108 to staple 106.

Accordingly, elongate recesses or apertures 107 function in part to guide protrusions 111 and therefore legs 110 of backbone 108 along staple 106 during a staple locking operation and in part cooperate with ribs or fins 113 to lock backbone 108 to staple 106. As shown in FIGS. 13 and 14, a push bar 112 is provided inside inner tubular member 74 for engaging backbone 108 along a proximal side thereof and for pushing the backbone onto staple 106 in a distally directed stroke of push bar 112.

Staple 106 is provided at the distal or free end of each staple leg 114 with at least one tooth or barb 116 for facilitating the gripping of tissue by the staple. The distal ends of applicator jaws 76 are preferably pointed for enabling the jaws to enter targeted tissue. As discussed above with reference to the first embodiment of a staple applicator device, jaws 76 are provided along mutually facing surfaces with grooves 118 for seating staple 106 and allowing for backbone 108 to slide over the closed staple.

Jaws 76 are attached to a drive mechanism in handle 72 (FIG. 13A) that opens and closes the jaws in response pressure placed on a trigger 120 by an operator. During a staple deployment procedure, thumb wheel 98 is rotated to assist in correct positioning of the stapler jaws 76 relative to a target tissue structure. Trigger 120 is pressed to close jaws 76 and concomitantly staple 106. If the position is not optimal, the pressure on trigger 120 may be released to enable repositioning of jaws 76 and staple 106. A ratchet actuator 122 may be provided on handle 72 for use in an over-travel situation, so that it is not necessary to release trigger 120 every time during the positioning process. Push bar 112 is translated in the distal direction by pressing a button 124 on a rear side of handle 72.

The forward or distally directed motion of outer tubular member 82 and jaws-closing sleeve 84 is arrested when pin 96 comes into contact with distal end 94 of slot 90. During the forward motion of outer tubular member 82 and jaws-closing sleeve 84, three pieces undergo elastic deformation, namely, springs 80 and staple 106.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An endoscopic clip applicator device comprising a. an elongate inner tubular member with a clevis at a distal end thereof; and b. said clevis configured with a pair of distally extending noses, said noses provided with apertures for receiving respective pivot pins; and c. two jaws pivotally mounted to said clevis, whereby said jaws turn about said pivot pins; and d. said jaws being spring biased in an open configuration; and e. an outer tubular member with a sleeve at a distal end thereof, said sleeve provided with two open slots, defining two opposed fingers, said fingers being engageable with said jaws to pivot said jaws toward one another during a distally directed stroke motion of said outer tubular member.

2. The device defined in claim 1 wherein said outer tubular member comprises an elongate coil and a sleeve provided at a distal end of said coil, said open slots and said fingers being provided on a distal side of said sleeve.

3. The device defined in claim 2 wherein said sleeve is provided with a longitudinal slot, closed at a proximal end and a distal end, defining a range of longitudinal motion of said sleeve and said outer tubular member, a pin fastened to said inner tubular member at least partially traversing said slot to limit longitudinal motion of said outer tubular member and said sleeve relative to said inner tubular member and to rotationally entrain said outer tubular member to said inner tubular member.

4. The device defined in claim 3 wherein at least one spring member is provided in contact with said jaws for biasing same towards said open configuration.

5. The device defined in claim 4 wherein said clevis is provided with a recessed seat proximal of said jaws, said spring member being located in part in said seat.

6. The device defined in claim 5 wherein said spring member includes a coiled portion, said coiled portion being disposed in said seat.

7. The device defined in claim 1, further comprising a staple disposed between said jaws, said staple having notches, recesses or apertures for receiving and securing a backbone locking element.

8. The device defined in claim 7 wherein said backbone is made of rigid material having a pair of legs slidable over a backside of said staple and securable firmly over the staple to hold the same in a closed configuration, said legs having inwardly extending protrusions engageable in respective ones of said notches, recesses or apertures for locking said legs into place over said staple.

9. The device defined in claim 8 wherein said staple is provided along said backside with channels for guiding said legs of said backbone along the staple so that said protrusions are received in said notches, recesses, or apertures.

10. The device defined in claim 7, further comprising a push bar operatively engageable with said backbone and extending through said inner tubular member for pushing said backbone onto said staple.

11. The device defined in claim 1 wherein distal ends of said jaws are pointed for enabling said jaws to enter targeted tissue, said jaws being provided along mutually facing surfaces with grooves for seating a staple and allowing for a backbone to slide over the closed staple.

12. The device defined in claim 1 wherein said jaws are attached to a drive mechanism that opens and closes said jaws, said drive mechanism being attached to a handle mechanism.

* * * * *